US00PP15356P2

(12) United States Plant Patent
van der Zwet

(10) Patent No.: US PP15,356 P2
(45) Date of Patent: Nov. 23, 2004

(54) *LYSIMACHIA* PLANT NAMED 'JUMBO'

(50) Latin Name: *Lysimachia fortunei*×*Lysimachia clethroides*
Varietal Denomination: Jumbo

(76) Inventor: Alexius Johannes Joseph van der Zwet, De Baan 17, 2377 CA Oude Wetering (NL)

( * ) Notice: Subject to any disclaimer, the term of this patent is extended or adjusted under 35 U.S.C. 154(b) by 0 days.

(21) Appl. No.: 10/783,349

(22) Filed: Feb. 21, 2004

(51) Int. Cl.[7] ..... A01H 5/00
(52) U.S. Cl. ..... Plt./263
(58) Field of Search ..... Plt./263

(56) References Cited

U.S. PATENT DOCUMENTS

PP13,547 P3 * 2/2003 Crowther et al. ..... Plt./263

OTHER PUBLICATIONS

UPOV ROM GTITM Computer Database 2004/02, GTI Jouve Retrieval Software Citations for 'Jumbo'.*

* cited by examiner

*Primary Examiner*—Bruce R. Campell
*Assistant Examiner*—W C Haas
(74) *Attorney, Agent, or Firm*—C. A. Whealy

(57) ABSTRACT

A new and distinct cultivar of *Lysimachia* plant named 'Jumbo', characterized by its tall and erect flowering stems; dark green-colored leaves; large curving flowering racemes; large white-colored flowers; and good postproduction longevity.

2 Drawing Sheets

Botanical classification/cultivar designation: *Lysimachia fortunei*×*Lysimachia clethroides* cultivar Jumbo.

BACKGROUND OF THE INVENTION

The present Invention relates to a new and distinct cultivar of *Lysimachia* plant, botanically known as *Lysimachia fortunei*×*Lysimachia clethroides*, and hereinafter referred to by the name 'Jumbo'.

The new *Lysimachia* is a product of a planned breeding program conducted by the Inventor in Oude Wetering, The Netherlands. The objective of the breeding program was to develop new cut *Lysimachia* cultivars with large flowers with attractive foliage and flower coloration and good postproduction longevity.

The new *Lysimachia* originated from a cross-pollination made by the Inventor in 1999 in Oude Wetering, The Netherlands of an unidentified selection of *Lysimachia fortunei,* not patented, as the female, or seed, parent and an unidentified selection of *Lysimachia clethroides*, not patented, as the male, or pollen, parent. The new *Lysimachia* was discovered and selected by the Inventor in 2000 as a flowering plant within the progeny of the stated cross-pollination in a controlled environment in Oude Wetering, The Netherlands. The selection of this new *Lysimachia* was based on its large flowers and attractive foliage and flower coloration.

Asexual reproduction of the new cultivar by cuttings taken in a controlled environment in Oude Wetering, The Netherlands since 2001, has shown that the unique features of this new *Lysimachia* are stable and reproduced true to type in successive generations of asexual propagation.

SUMMARY OF THE INVENTION

Plants of the cultivar Jumbo have not been observed under all possible environmental conditions. The phenotype may vary somewhat with variations in environment such as temperature and light intensity without, however, any variance in genotype.

The following traits have been repeatedly observed and are determined to be the unique characteristics of 'Jumbo'. These characteristics in combination distinguish 'Jumbo' as a new and distinct cultivar:

1. Tall and erect flowering stems.
2. Dark green-colored leaves.
3. Large curving flowering racemes with large white-colored flowers.
4. Good postproduction longevity.

Plants of the new *Lysimachia* are most similar to plants of the parent selections. Plants of the new *Lysimachia* differ primarily from plants of the female parent selection in the following characteristics:

1. Plants of the new *Lysimachia* have larger racemes than plants of the female parent selection.
2. Plants of the new *Lysimachia* have larger flowers than plants of the female parent selection.

Plants of the new *Lysimachia* differ primarily from plants of the male parent selection in the following characteristics:

1. Plants of the new *Lysimachia* have darker green-colored leaves than plants of the male parent selection.
2. Plants of the new *Lysimachia* have larger racemes than plants of the male parent selection.
3. Plants of the new *Lysimachia* have larger flowers than plants of the male parent selection.
4. Plants of the new *Lysimachia* flower in June in The Netherlands whereas plants of the male parent selection flower in July in The Netherlands.

BRIEF DESCRIPTION OF THE PHOTOGRAPHS

The accompanying colored photographs illustrate the overall appearance of the new *Lysimachia*, showing the colors as true as it is reasonably possible to obtain in colored reproductions of this type. Colors in the photographs may differ slightly from the color values cited in the detailed botanical description which accurately describe the colors of the new *Lysimachia.*

The photograph on the first sheet is a view of a field of typical flowering plants of 'Jumbo'.

The photograph on the second sheet is a close-up view of a typical flowering raceme and leaves of 'Jumbo'.

DETAILED BOTANICAL DESCRIPTION

The aforementioned photographs, following observations, measurements and values describe plants of the new *Lysimachia* grown in Aalsmeer, The Netherlands in an outdoor cultivated field during the summer. During the production of the plants, day temperatures ranged from 18 to 25° C. and night temperatures ranged from 15 to 18° C. Plants used for the photographs and description were about one year old.

Color references are made to The Royal Horticultural Society Colour Chart, 1995 Edition, except where general terms of ordinary dictionary significance are used.

Botanical classification: *Lysimachia fortunei*×*Lysimachia clethroides* cultivar Jumbo.

Parentage:

*Female parent.*—Unidentified selection of *Lysimachia fortunei*, not patented.

*Male parent.*—Unidentified selection of *Lysimachia clethroides*, not patented.

Propagation:

*Type.*—By cuttings.

*Time to initiate roots.*—Summer: About 7 days at 20° C. Winter: About 10 days at 19° C.

*Time to produce a rooted young plant.*—Summer: About 21 days at 20° C. Winter: About 28 days at 19° C.

*Root description.*—Fibrous; white in color.

*Rooting habit.*—Freely branching.

Plant description:

*Plant/growth habit.*—Narrowly upright, tall and erect flowering stems; moderately vigorous.

*Flowering stem description.*—Quantity per plant: About four to six. Aspect: Erect. Length: About 70 to 80 cm. Spread: About 30 cm. Diameter: About 5 mm. Internode length: About 2 to 3 cm. Strength: Strong. Texture: Smooth, glabrous. Color: 138A.

*Foliage description.*—Arrangement: Opposite, simple, sessile. Length: About 12 cm. Width: About 5 cm. Shape: Oblong. Apex: Acute to acuminate. Base: Attenuate. Margin: Entire. Texture, upper and lower surfaces: Smooth, glabrous. Venation pattern: Pinnate. Color: Developing foliage, upper surface: 143C. Developing foliage, lower surface: 143D. Fully expanded foliage, upper surface: 141A. Fully expanded foliage, upper surface: 141C. Venation, upper surface: 143C. Venation, lower surface: 143D.

Flower description:

*Flower type and habit.*—Large, single, rounded and white-colored flowers arranged in large curving terminal racemes; flowers face mostly outward. Flowers persistent. Racemes about 10 cm in length and about 2 cm in diameter; about 50 flowers per raceme. Natural flowering season: Towards the end of June in The Netherlands.

*Fragrance.*—None detected.

*Flower longevity on the plant.*—About 14 days.

*Flower longevity as a cut flower.*—About 10 days.

*Flower buds.*—Length: About 3 mm. Diameter: About 3 mm. Shape: Ovoid. Color: 145C.

*Flower diameter.*—About 1 cm.

*Flower height* (*depth*).—About 1 cm.

*Petals.*—Quantity per flower: Five, not fused. Length: About 5 mm. Width: About 3 mm. Shape: Deltoid. Apex: Acute. Margin: Entire. Texture: Smooth, glabrous. Color: When opening, upper and lower surfaces: 155D. Opened flower, upper and lower surfaces: 155D.

*Sepals.*—Quantity per flower: Five, fused at the base. Length: About 1 mm. Width: About 1 mm. Shape: Deltoid. Apex: Acute. Margin: Entire. Texture: Smooth, glabrous. Color, upper and lower surfaces: 145C.

*Pedicels.*—Angle: About 90° from stem. Strength: Strong. Length: About 2 mm. Diameter: About 1 mm. Color: 145C.

*Reproductive organs.*—Stamens: Quantity per flower: One. Anther shape: Oblong. Anther length: Less than 1 mm. Anther color: 143D. Pollen amount: Moderate. Pollen color: 152C. Pistils: Quantity per flower: One. Pistil length: Less than 1 mm. Stigma color: 143D. Style length: Less than 1 mm. Style color: 143D. Ovary color: 145D.

*Seed/fruit.*—Plants of the new *Lysimachia* have not been observed to produce fruits and seeds to date.

Disease/pest resistance: Plants of the new *Lysimachia* has not been observed to be resistant to pathogens and pests common to *Lysimachias*.

Temperature tolerance: Plants of the new *Lysimachia* have been observed to tolerate temperatures from −20 to 30° C.

It is claimed:

1. A new and distinct cultivar of *Lysimachia* plant named 'Jumbo', as illustrated and described.

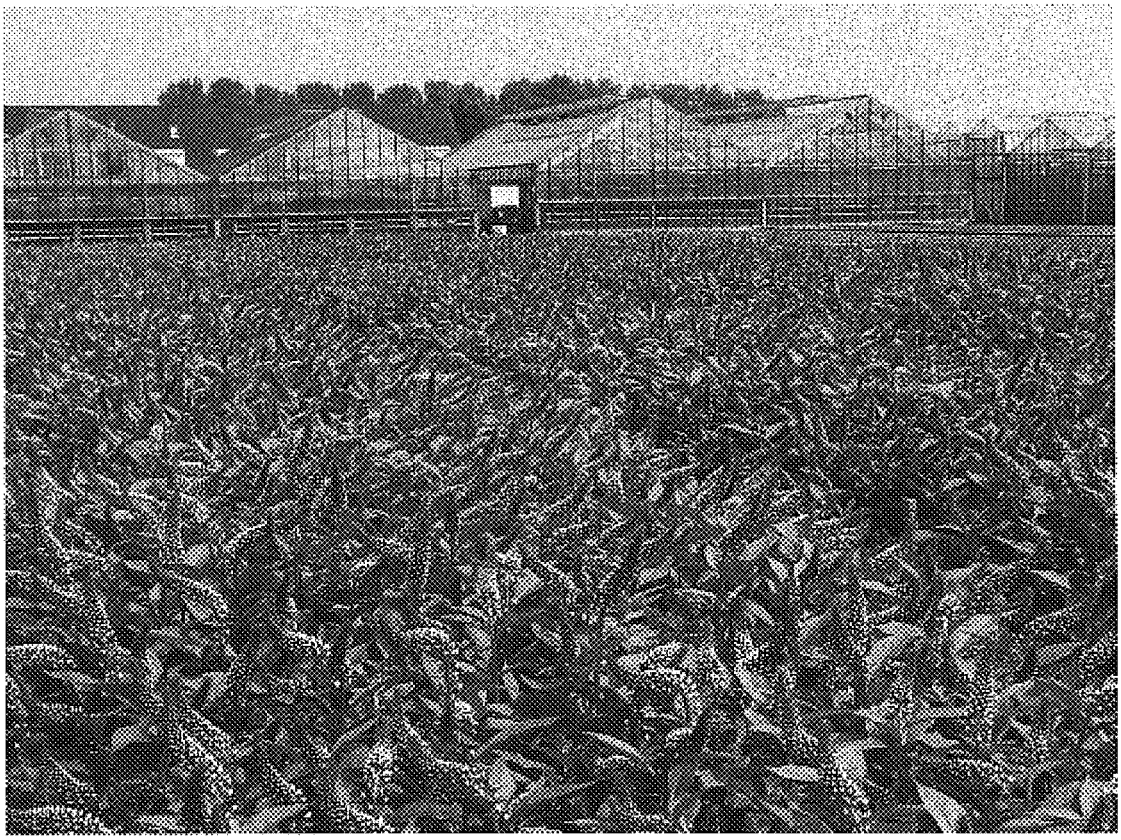

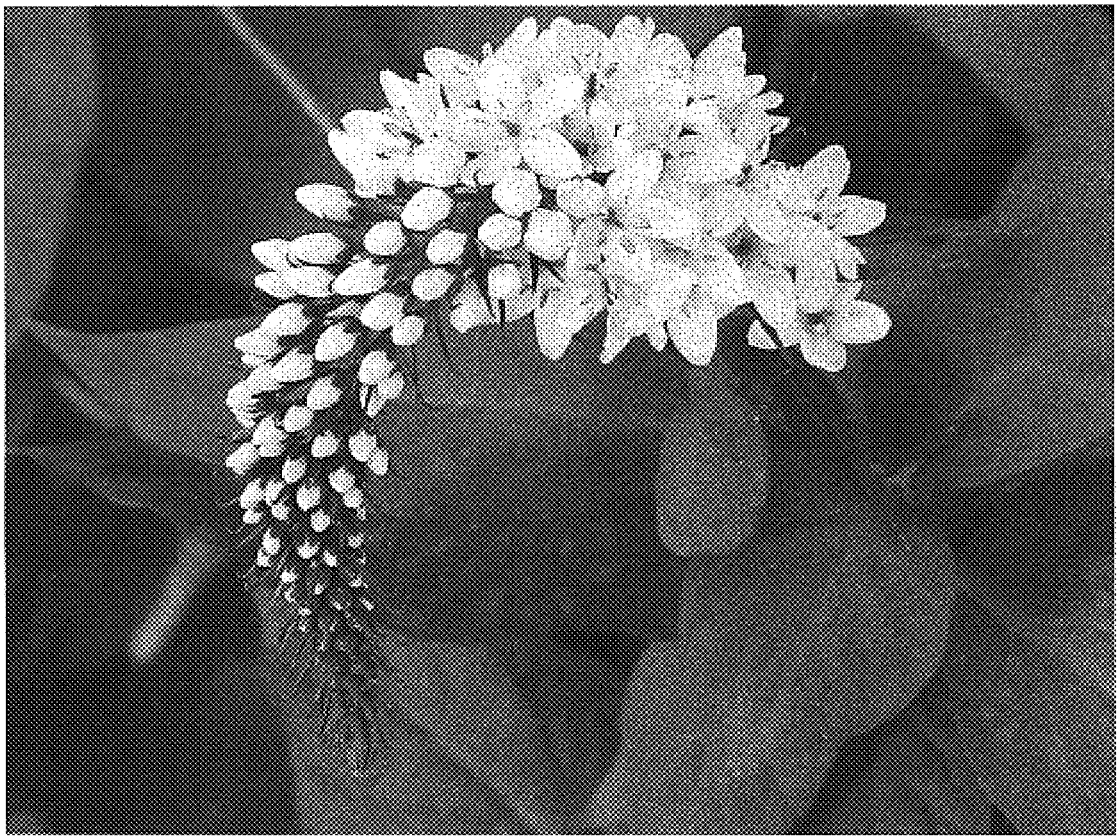

* * * * *